United States Patent [19]
Page

[11] 4,015,124
[45] Mar. 29, 1977

[54] DETERMINING THE CONCENTRATION OF SULPHUR IN COAL

[75] Inventor: Dennis Page, Gateshead, England

[73] Assignee: Coal Industry (Patents) Limited, London, England

[22] Filed: Feb. 20, 1976

[21] Appl. No.: 659,972

[30] Foreign Application Priority Data

Mar. 14, 1975 United Kingdom ............ 10713/75

[52] U.S. Cl. .............................................. 250/273
[51] Int. Cl.$^2$ ...................................... G01N 23/00
[58] Field of Search ........... 250/272, 273, 274, 252

[56] References Cited

UNITED STATES PATENTS

| | | | |
|---|---|---|---|
| 3,467,824 | 9/1969 | Boyce et al. ....................... | 250/273 |
| 3,671,744 | 6/1972 | Constantine ....................... | 250/273 |

FOREIGN PATENTS OR APPLICATIONS 1,177,067   1/1970   United Kingdom

Primary Examiner—Alfred E. Smith
Assistant Examiner—B. C. Anderson
Attorney, Agent, or Firm—James C. Wray

[57] ABSTRACT

This invention relates to a method for determining the concentration of sulphur in coal and to apparatus which enables this method to be put into practice. The method involves measuring the intensities of the X-ray fluorescent radiations from iron and sulphur atoms in a sample of coal which has been excited by X-ray radiation. The measures of the intensities are combined mathematically to give an output from which the concentration of sulphur in the coal may be determined. Using the apparatus described the concentration of sulphur in a sample of coal can be determined quickly and accurately by an unskilled worker.

15 Claims, 1 Drawing Figure

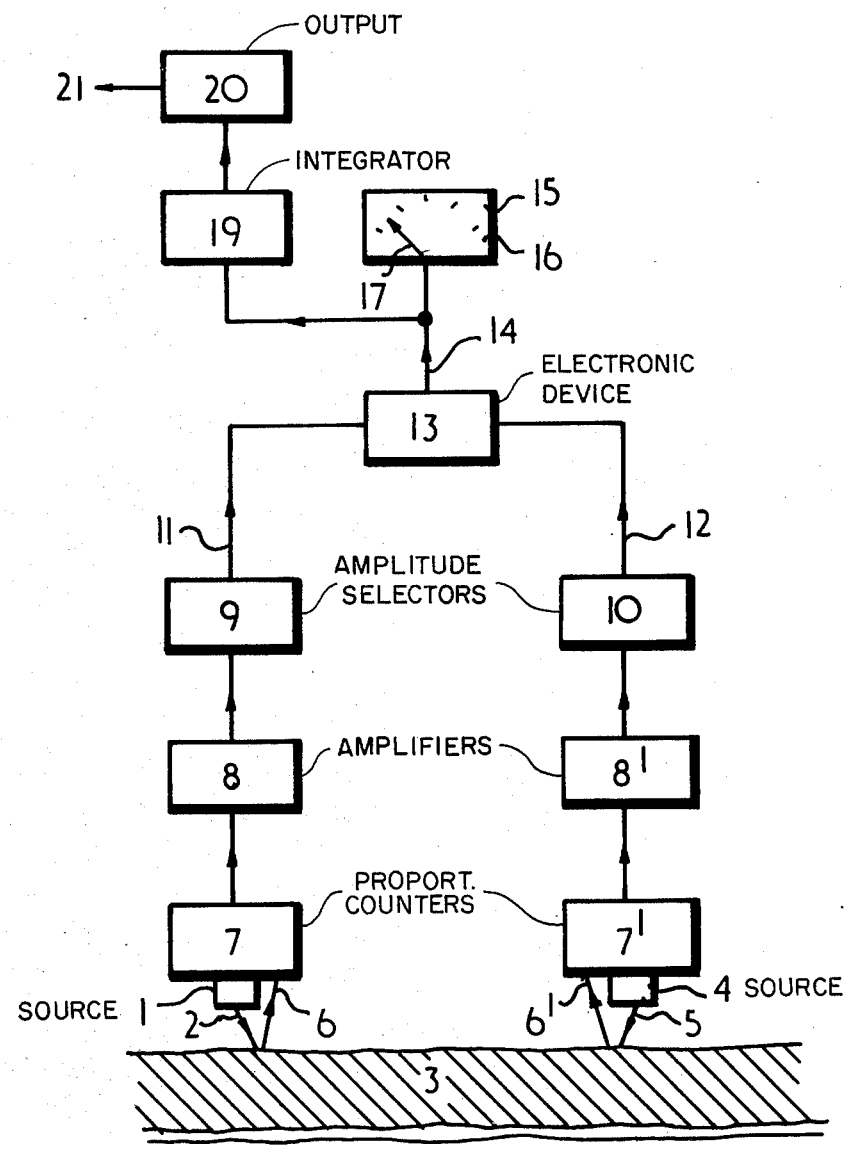

DETERMINING THE CONCENTRATION OF SULPHUR IN COAL

This invention relates to a method of determining the concentration of sulphur in coal.

It is necessary to know the sulphur content of a given batch of coal in order to be able to supply the correct type of coal for a given use. For instance coal-burning power stations will only accept coal with a low sulphur content. Coals with low sulphur contents are also preferred for use in domestic solid-fuel burning heating systems.

Previously the sulphur content of a batch of coal has been measured by chemically analysing a sample. This process is time consuming and there is a delay between mining the batch and despatching it either to the appropriate storage bunker or to the appropriate user. This delay involves the inefficient use of intermediate storage containers.

It is therefore an object of the present invention to provide a method of determining the concentration of sulphur in coal which is easily and quickly operable, and can be applied to the coal as it is mined.

A suitable technique for adaption for this purpose is X-ray fluorescence spectroscopy. When an atom is irradiated with high energy electromagnetic radiation (X-rays) of the appropriate energy its inner electron shells are disturbed and a characteristic fluorescence is observed. The fluorescent radiation has an energy also in the X-ray range and this energy is proportional to the square of the atomic number of the atom, irrespective of the chemical state of combination of the atom. The intensity of the fluorescent radiation is approximately proportional to the concentration of the atom in the matrix. For elements of atomic number 20 and above this is an easily applicable technique. However, for elements such as sulphur (atomic number = 16), the fluorescent radiation is of such an energy that it can be absorbed by other elements of low atomic number such as silicon, aluminium and iron in a matrix and a small variation in the concentration of these elements in a matrix can cause considerable variations in the intensity of the characteristic fluorescent radiation leaving samples having the same sulphur content. These absorbing elements are commonly found in the ash-forming minerals in coals in amounts which vary considerably from batch to batch. Therefore the determination of the sulphur concentration of the coal by measurement of the itensity of its characteristic fluorescent radiation can be in considerable error.

Sulphur occurs in coal in three forms, viz organic, sulphatic and pyritic (i.e. as iron pyrites), while iron can be classified in coal as either pyritic or non pyritic. The concentration of the sulphur in the coal can be expressed as follows:-

$$S = (Fe - Fe_n) \cdot K_1 + S_0 + S_s$$

Where:-
$S$ = cencentration of sulphur in coal
$Fe$ = cencentration of iron in coal
$Fe_n$ = cencentration of non-pyritic iron in coal
$K_1$ = conversion factor to determine the concentration of sulphur in pyritic form (= 1.1481)
$S_0$ = concentration of sulphur in organic form
$S_s$ = concentration of sulphur in sulphatic form Determination of the concentration of iron (atomic number = 26) in coal by the excitation of its characteristic fluorescent radiation is relatively easy since the higher energy radiation is much less absorbed by the ash-forming minerals. Unfortunately, however, the values of $Fe_n$, $S_0$ and $S_s$ are generally not constant.

We have found that for a given type of coal, the concentration of sulphur in the coal can be reasonably accurately expressed as a function of the intensities of the characteristic fluorescent radiations emitted by the iron and sulphur in a sample of the coal when the sample is bombarded with electromagnetic radiation of appropriate energy.

In particular, we have found that to a good approximation:-

$$S = a + bX + cY$$

Where:-
$S$ = concentration of sulphur in the coal sample;
$X$ = intensity of fluorescent radiation emitted by the sulphur in the sample;
$Y$ = intensity of fluorescent radiation emitted by the iron in the sample; and
$a$, $b$ and $c$ are constants.

The values of $a$, $b$ and $c$ depend on the test apparatus and the type of coal under test and are determined by placing standard samples of the type of coal under test in the test apparatus.

The sulphur content of an unknown sample may then be determined by measuring the values of X and Y and combining them as indicated above.

It is envisaged that more complex mathematical relationships between S, X and Y may result in S being determined more accurately.

Accordingly, the present invention provides a method for continuously determining the concentration of sulphur in coal, which method includes the steps of bombarding a sample of coal with electromagnetic radiation in the X-ray region of the spectrum to cause the iron and the sulphur atoms in the sample to emit their respective characteristic fluorescent radiations detecting said fluorescent radiations, measuring the intensities of said fluorescent radiations and combining said intensities or measures mathematically to produce an output from which the concentration of sulphur in the sample may be determined.

For certain types of coal (hereinafter referred to as 'coal of the type described') the values of $Fe_n$, $S_0$ and $S_s$ are substantially constant.

In order to determine the concentration of sulphur in coal of the type described the present invention provides a method which includes the steps of bombarding a sample of the coal with electromagnetic radiation in the X-ray region of the spectrum to cause the iron atoms in the sample to emit their characteristic fluorescent radiation, detecting said fluorescent radiation, measuring the intensity of said fluorescent radiation, from which measure the concentration of iron in the sample is calculated, correcting the concentration of iron to allow for any non-pyritic iron in the coal, determining the concentration of sulphur present in the coal as iron pyrites from the corrected concentration of iron and correcting the concentration of sulphur thus found to allow for sulphur present in organic and sulphatic form to give the concentration of sulphur in the coal.

Once the concentration of iron in the sample has been determined the sulphur content could be calculated by hand. However, in view of the linear relationship between the concentration of iron and the concentration of sulphur in coal of the type described and since the intensity of fluorescent rdiation from the iron is approximately directly proportional to the concentration of iron in the coal, it will be appreciated that the scale of a linear intensity meter could be recalibrated to give a direct reading of the sulphur content of any sample, the value of the constant($S_0 + S_s - Fe_n K_1$) for any given type of coal being inserted in the meter by adjusting the scale with respect to the rest position of the needle of the meter.

In order to determine the sulphur content of a large quantity of coal batch sampling may be used. However, continuous sampling is preferable to minimise heterogeneity effects.

Continuous sampling may be achieved using an apparatus as described in British Patent No. 1,177,067 or any other suitable apparatus.

It is preferred that the sample is ground to a diameter of smaller than 0.5 mm. For coals with low ash content the maximum diameter can be 1 mm. For coals of the type described it is possible to use particles with a diameter of up to 25 mm, but it is peferred that the diameter should not exceed 5 mm.

It is necessary, in order to excite both the iron and sulphur fluorescent radiations, for the exciting electromagnetic radiation to have energies in the ranges of 2.5 to 7.0 keV and 7.2 to 25 keV. These radiations may be provided either by separate isotope sources, or by a "bremsstrahlung" source, or by an X-ray tube. It is preferred to use separate isotope sources since these are easier to handle. If a "bremsstrahlung" source is used a single semi-conductor detector (e.g. a lithium-drifted silicon detector system may be used.

An apparatus embodying the method of the invention will now be described, by way of example, with reference to the drawing accompanying the provisional specification, which shows a block diamgram of the apparatus.

A layer of coal particles 3 of the appropriate maximum diameter is carried on a continuously moving conveyor of the type described in B.P. 1,177,067 beneath two isotope sources 1 and 4. Source 1 comprises iron 55 (5.9 keV), and the radiation 2 from it excites sulphur atoms, and other atoms whose atomic numbers are close to that of sulphur. The fluorescent radiation and the back-scattered radiation 6 from the sample is detected by a proportional counter 7, which gives a signal which is amplified by amplifier 8 and transmitted to pulse amplitude selector 9, which is adjusted to select only those parts of the signal originating from the sulphur in the sample. The selected signal on line 11 leaving the pulse-amplitude-selector 9 is then fed to an electronic device 13 as hereinafter described.

Simultaneously or consecutively, the sample passes under source 4 which comprises plutonium 238 (14 − 17 keV), the radiation 5 from which excites the iron atoms. The fluorescent radiation and the backscattered radiation 6' from the sample is detected by proportional counter 7', to give a signal which is amplified by amplifier 8' and transmitted to pulse-amplitude selector 10 which is adjusted to select only those parts of the signal originating from the iron present in the sample. The selected signal on line 12 leaving pulse-amplitude selector 10 is then combined with the signal on line 11 in electronic device 13 according to the formula:-

$$S = a + bX + cY$$

where $a$, $b$ and $c$ are constants, and X and Y are the magnitudes of signals 11 and 12 respectively. Constants $a$, $b$ and $c$ are determined by calibrating the apparatus with standard samples of coal of the type under test. The output signal on line 14 from the electronic device 13 is then fed to meter 15, having a linear scale 16 and a pointer 17. The combining means is shown as electronic device 13, a computer programmed to compute and produce an output as an electric signal indicating the concentration of sulphur in the coal.

The signal on line 14 may also be fed to an integrator 19 arranged to produce a digital output 20 at desired intervals and to transmit an output signal on line 21 to operate apparatus for directing the batch from which the sample particles were taken into an appropriate bunker according to its sulphur content.

If a coal of the type described is being sampled the source 1, detector 6, amplifier 8, pulse amplitude selector 9 and electronic device 13 are disconnected and the signal from the pulse amplitude selector 10 is fed directly to the meter 15, calibrated to display the sulphur concentration or to the integrator 19.

The apparatus described above is easy to use and can be operated by an unskilled worker at the pit head. The results obtained using the described method are more consistent and accurate than any previously used non-chemical method, and are obtained much more quickly than by use of chemical methods.

I claim:

1. A method for continuously measuring the concentration of sulphur in coal, including the steps of bombarding a sample of coal with electromagnetic radiation in the X-ray region of the spectrum to cause the iron and sulphur atoms in the sample to emit their characteristic fluorescent radiations, detecting said fluorescent radiations, measuring the intensities of said fluorescent radiations, and combining the measures mathematically to produce an output from which the concentration of sulphur in the sample may be determined.

2. A method according to claim 1 in which the intensities of said fluorescent radiations are measured separately before being combined mathematically to produce an output from which the concentration of sulphur in the sample may be determined.

3. A method for continuously measuring the concentration of sulphur in coal of the type described, including the steps of bombarding a sample of coal with electromagnetic radiation in the X-ray region of the spectrum to cause the iron atoms in the sample to emit their characteristic fluorescent radiation, detecting said fluorescent radiation, measuring the intensity of said fluorescent radiation, from which measure the concentration of iron in the sample is calculated, correcting the concentration of iron to allow for non-pyritic iron in the coal, determining the concentration of sulphur present in the coal as iron pyrites from the corrected concentration of iron, and correcting the concentration of sulphur thus found to allow for sulphur present in the coal in organic and sulphatic form to give the concentration of sulphur in the coal.

4. An apparatus for determining the concentration of sulphur in coal which comprises
   a. A source of X-ray radiation for irradiating the sample with X-ray radiation to cause the iron and sulphur atoms in the sample to emit their respective characteristic fluorescent radiations,
b. detectors for detecting said fluorescent radiations,
c. measuring means for measuring the intensities of said fluorescent radiations,
d. combining means for combining mathematically said measures of said intensities to produce an output,
e. determining means for determining from said output the concentration of sulphur in the sample.

5. An apparatus according to claim 4 in which the source of X-ray radiation is an X-ray tube.

6. An apparatus according to claim 4 in which the source of X-ray radiation is a radio-isotope.

7. An apparatus according to claim 4 in which the detectors of said fluorescent radiations is a proportional counter.

8. An apparatus according to claim 7 in which the measuring means are pulse amplitude selectors.

9. An apparatus according to claim 8 in which the combining means is a means to produce an output as an electrical signal indicating the concentration of sulphur in the coal.

10. An apparatus for determining the concentration of sulphur in coal of the type described which comprises a. a source of X-ray radiation for irradiating the sample with X-ray radiation to cause the iron atoms in the sample to emit their characteristic fluorescent radiation.
b. detectors for detecting said fluorescent radiation,
c. measuring means for measuring the intensity of said fluorescent radiation,
d. determining means for determining from said measure of said intensity the concentration of sulphur in the sample.

11. An apparatus according to claim 10 in which the source of X-ray radiation is an X-ray tube.

12. An apparatus according to claim 10 in which the source of X-ray radiation is a radio-isotope.

13. An apparatus according to claim 10 in which the detectors of said fluorescent radiation is a proportional counter.

14. An apparatus according to claim 13 in which the measuring means is a pulse amplitude selector.

15. A method according to claim 1 wherein the combining step comprises combining the measures mathematically according to the formula:

$$S = a + bX + cY$$

where $a$, $b$ and $c$ are constants, and $X$ and $Y$ are the measured intensities of fluorescent radiation emitted respectively by sulfur and by iron in the sample, and wherein $S$ is the sulfur content in the sample.

* * * * *